United States Patent
Portnoy et al.

(10) Patent No.: US 10,115,171 B2
(45) Date of Patent: Oct. 30, 2018

(54) MEDICATION RELATED TASK NOTIFICATION SYSTEM

(75) Inventors: Alan M. Portnoy, Warwick, PA (US); Deborah Saeger, Allentown, PA (US)

(73) Assignee: Cerner Innovation, Inc., Kansas City, KS (US)

(*) Notice: Subject to any disclaimer, the term of this patent is extended or adjusted under 35 U.S.C. 154(b) by 1715 days.

(21) Appl. No.: 12/165,736

(22) Filed: Jul. 1, 2008

(65) Prior Publication Data

US 2009/0048868 A1 Feb. 19, 2009

Related U.S. Application Data

(60) Provisional application No. 60/948,788, filed on Jul. 10, 2007.

(51) Int. Cl.

| | |
|---|---|
| *G06Q 50/00* | (2012.01) |
| *G06Q 10/00* | (2012.01) |
| *G06F 19/00* | (2018.01) |
| *A61B 5/00* | (2006.01) |
| *G06Q 50/22* | (2018.01) |
| *G06Q 10/06* | (2012.01) |
| *G06Q 10/10* | (2012.01) |
| *G06F 17/30* | (2006.01) |

(52) U.S. Cl.
CPC ....... *G06Q 50/22* (2013.01); *G06F 17/30663* (2013.01); *G06F 19/00* (2013.01); *G06Q 10/06316* (2013.01); *G06Q 10/10* (2013.01)

(58) Field of Classification Search
CPC ....... G06Q 50/22; G06Q 50/24; G06F 19/322
USPC ........................................................ 705/2–3
See application file for complete search history.

(56) References Cited

U.S. PATENT DOCUMENTS

| | | |
|---|---|---|
| 7,230,529 B2 | 6/2007 | Ketcherside, Jr. et al. |
| 8,050,946 B2 | 11/2011 | Hertel et al. |
| 2004/0010425 A1 | 1/2004 | Wilkes et al. |
| 2004/0021693 A1 | 2/2004 | Monteleone |
| 2004/0078231 A1 | 4/2004 | Wilkes et al. |
| 2004/0172283 A1 | 9/2004 | Vanderveen et al. |

(Continued)

FOREIGN PATENT DOCUMENTS

WO    WO2007111910    10/2007

*Primary Examiner* — Joy Chng
(74) *Attorney, Agent, or Firm* — Shook, Hardy & Bacon L.L.P.

(57) ABSTRACT

A task management system for informing a clinician of medication administration related tasks to be performed, includes a repository of information. The repository of information associates data identifying multiple different medications with corresponding multiple post-administration alert messages. An individual alert message notifies a clinician of a particular post-administration task to be performed concerning a particular medication following administration of the particular medication to a patient. An input processor receives data indicating the particular medication has been administered to the patient. A workflow processor, in response to received data indicating the particular medication has been administered to the patient, uses the repository for identifying a post-administration task associated with the particular medication and automatically adds data indicating the post-administration task to be performed to a task list of a clinician. A reproduction device presents the post-administration task and task list of the clinician for viewing by a user.

14 Claims, 4 Drawing Sheets

(56) References Cited

U.S. PATENT DOCUMENTS

| | | |
|---|---|---|
| 2004/0199405 A1 | 10/2004 | Harper et al. |
| 2004/0204910 A1 | 10/2004 | Brumbach et al. |
| 2004/0243444 A1* | 12/2004 | Steusloff et al. ............ 705/2 |
| 2005/0021368 A1* | 1/2005 | Burkeen et al. ............ 705/2 |
| 2006/0026205 A1 | 2/2006 | Butterfield |
| 2006/0106647 A1 | 5/2006 | Brummel et al. |
| 2006/0149416 A1 | 7/2006 | Mahapatra et al. |
| 2007/0033075 A1 | 2/2007 | Hoffman et al. |
| 2007/0088458 A1 | 4/2007 | Laughland et al. |
| 2007/0168223 A1 | 7/2007 | Fors et al. |
| 2007/0203755 A1* | 8/2007 | Willson et al. ............ 705/3 |
| 2008/0065424 A1 | 3/2008 | Frick |
| 2008/0082366 A1 | 4/2008 | Miller et al. |
| 2008/0097792 A1 | 4/2008 | Marge |
| 2009/0138286 A1 | 5/2009 | Linder et al. |
| 2009/0164238 A1 | 6/2009 | Auchinleck |
| 2009/0222746 A1 | 9/2009 | Chirica et al. |
| 2010/0063847 A1 | 3/2010 | Eisenberg et al. |
| 2010/0241456 A1 | 9/2010 | Miller et al. |

\* cited by examiner

MEDICATION RELATED TASK NOTIFICATION SYSTEM

This is a non-provisional application of provisional application Ser. No. 60/948,788 filed Jul. 10, 2007, by A. M. Portnoy et al.

FIELD OF THE INVENTION

This invention concerns a task management system for informing a clinician of medication administration related tasks to be performed by automatically adding data indicating post-administration tasks to be performed to a task list of a clinician.

BACKGROUND OF THE INVENTION

The complexities associated with medication management have increased significantly over time with specific therapies requiring multiple follow ups and actions based upon physiologic responses, laboratory data and hospital policies, for example. A clinician can be overwhelmed with tasks that need to be performed to support the safe and affective administration of medications to patients. This can lead to delays in therapy and increased patient morbidity.

The problem is managed in known systems by entering reminder messages as entries in a drug database. Consequently, when a drug requiring routine follow up is entered in to a pharmacy system, a second order is entered that contains one or more reminder messages. These messages appear on a BPOC (Bar-coding Point of Care) system as medications. A system according to invention principles addresses the deficiencies of known systems and related problems.

SUMMARY OF THE INVENTION

The inventors have recognized that messages appearing on a BPOC (Bar-coding Point of Care) system as medications are not triggered to "pop-up" at specific times or conditions. Therefore, these reminders often go unnoticed by the clinician leading to lapses in care and potential harm to the patient. A system according to invention principles integrates a reminder/notification process within a BPOC system by identifying a specific message, stored within a medication database that may be used to alert the clinician of tasks or follow-up actions required for a particular medication. These messages are triggered to alert the clinician at specific times or under specific circumstances. A task management system for informing a clinician of medication administration related tasks to be performed, includes a repository of information. The repository of information associates data identifying multiple different medications with corresponding multiple post-administration alert messages. An individual alert message notifies a clinician of a particular post-administration task to be performed concerning a particular medication following administration of the particular medication to a patient. An input processor receives data indicating the particular medication has been administered to the patient. A workflow processor, in response to received data indicating the particular medication has been administered to the patient, uses the repository for identifying a post-administration task associated with the particular medication and automatically adds data indicating the post-administration task to be performed to a task list of a clinician. A reproduction device presents the post-administration task and task list of the clinician for viewing by a user.

DETAILED DESCRIPTION OF THE INVENTION

A system provides a reminder notification function integrated with a barcode point of care (BPOC) system, in which messages are associated with specific medications (within a medication or other database) and reduces the need for a clinician to handwrite message reminders that may be lost or inadvertently ignored. Reminder and notification messages are triggered to "pop-up" on a user display (PDA, notebook, phone, portable or fixed processing device), at specific times and under specific circumstances. These messages alert a clinician of tasks or follow-up actions that need to be performed and improve medication policy compliance, patient safety and clinical outcomes. The system generated message reminders are drug specific and are triggered to display to a clinician at critical times in a medication administration process. The generation of the messages is automatically activated in response to a pharmacist entering a medication order or validating a CPOE (Computerized Physician Order Entry) system order. A user of a BPOC system is presented with medication specific information when it is required, reducing the risk of information alert overload.

The system is used by nurses and other clinicians responsible for medication administration who utilize a BPOC system. During system set-up, users define order messages (for each medication) and determine an appropriate time during a medication administration workflow when individual messages are displayed to a clinician. The system enables clinicians to schedule dynamic generation of reminder messages whenever they are required and that alert a user of important follow-up tasks to be performed for a patient. The system includes a reminder and notification process that is medication specific in which messages may be tailored to the required actions of a particular medication or a specific combination of medications. Messages are triggered at specific times and under specific circumstances providing the right information at the right time (reducing information overload). Further, the information provided is more meaningful because it is displayed at the correct point in a workflow process so that it is not overlooked by a clinician. Alert messages are readily viewed and may require user follow up action data entry before the alert is removed (preventing advancing to a next step in an application, for example) until the alert is satisfied.

A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled to any other processor enabling interaction and/or communication therebetween. A display processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps (e.g., of FIG. 4) herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

A workflow processor, as used herein, processes data to determine tasks to add to or remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams.

Figure 1:
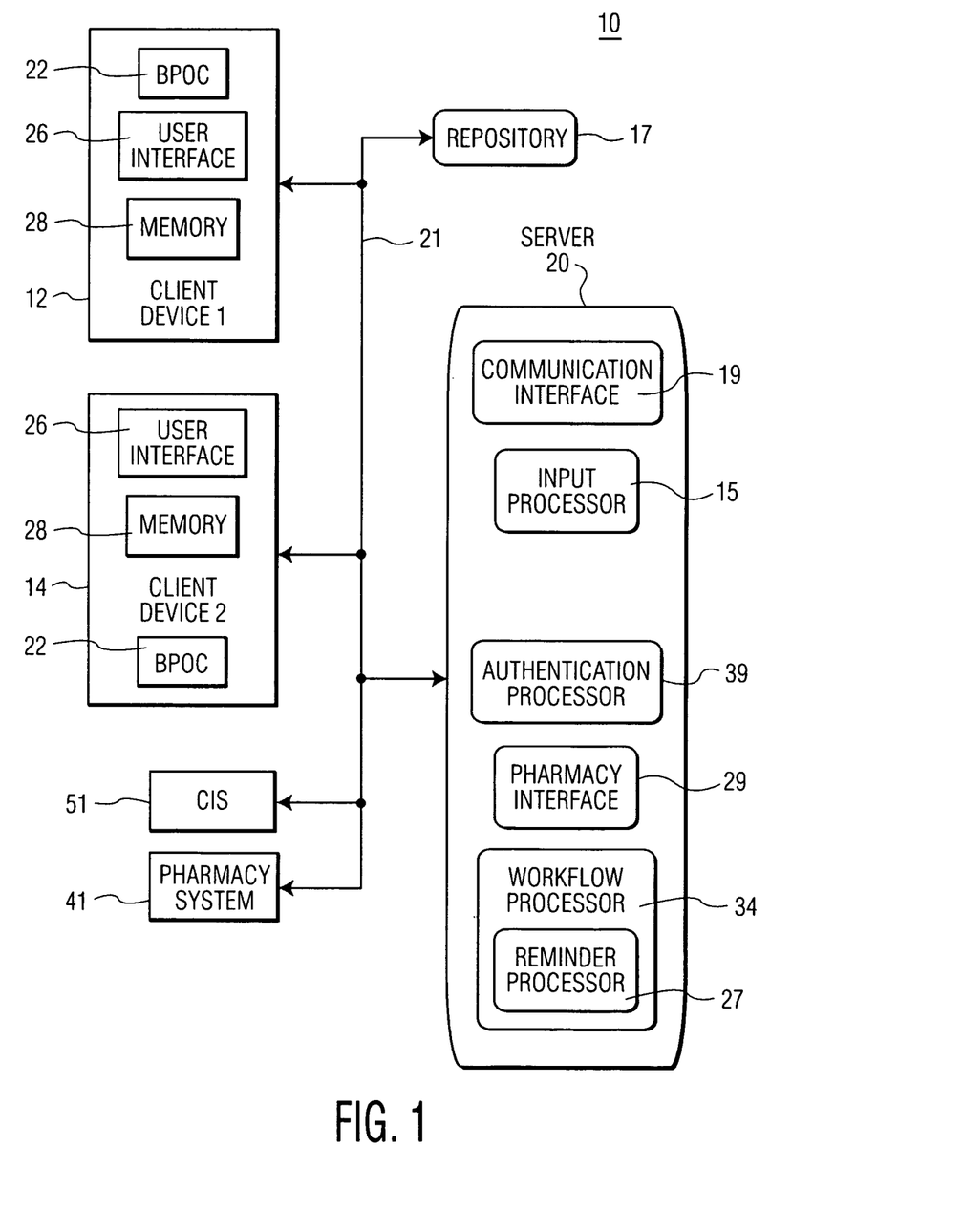
FIG. 1 shows a task management system for informing a clinician of medication administration related tasks to be performed, according to invention principles.

FIG. 1 shows task management system 10 for informing a clinician of medication administration related tasks to be performed. The term medication is used synonymously with the term drug herein. System 10 includes reproduction (processing) devices (e.g., workstations or portable devices such as notebooks, Personal Digital Assistants, cell phones) within mobile point of care units 12 and 14, at least one repository 17, Hospital Information System (HIS) 51 Application, Pharmacy Information System 41 and server 20, inter-communicating via network 21. Mobile point of care units 12 and 14 individually include memory 28, user interface 26 and a bar-code point of care system 22. User interface 26 provides data representing display images for presentation on mobile point of care unit 12 and 14. Server 20 includes input processor 15, communication interface 19, pharmacy interface 29, workflow processor 34 including Reminder processor 27 and authentication processor 39. Repository 17 includes information associating data identifying multiple different medications with corresponding multiple post-administration alert messages. Further, an individual alert message notifies a clinician of a particular post-administration task to be performed concerning a particular medication following administration of the particular medication to a patient. Input processor 15 receives data indicating the particular medication has been administered to the patient. Workflow processor 34 including Reminder processor 27, in response to received data indicating the particular medication has been administered to the patient, uses information in repository 17 to identify a post-administration task associated with the particular medication and automatically adds data indicating the post-administration task to be performed to a task list of a clinician. Reproduction devices (e.g., User Interface 26) in mobile point of care units 12 and 14 present the post-administration task and task list of the clinician for viewing by a user.

User interface 26 is located on a workstation at a point of care for initiating generation of data representing at least one display image enabling a clinician to access a task list in response to entered login information and to postpone addition of data indicating a post-administration task to a task list of the clinician. Pharmacy interface 29 receives order data concerning the patient from pharmacy information system 41. The order data associates the particular medication with the patient. Workflow processor 34 including Reminder processor 27 automatically adds data indicating the post-administration task is to be performed for the patient to a clinician task list in response to received order data. Authorization processor 39 enables access by a clinician to the task list in response to entered login information. User interface 26 presents one or more display images enabling a user to, initiate execution of Hospital information system 51 applications to provide a user with clinical application display images via mobile point of care unit 12. Workflow processor 34 including Reminder processor 27 initiates tracks and monitors task sequences involving patient medication administration tasks, in response to events.

Figure 2:
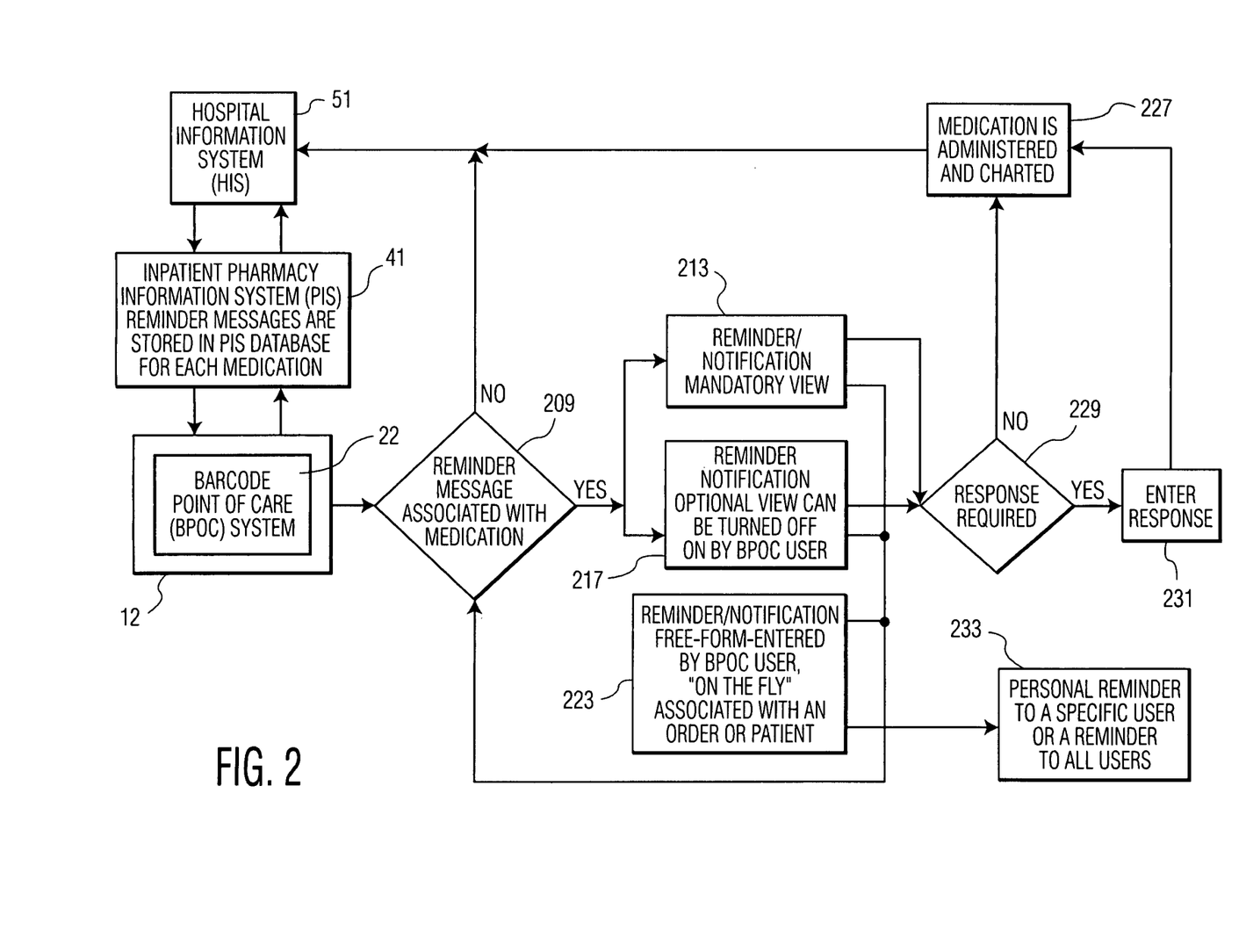
FIG. 2 shows medication administration related task flow in a system involving an HIS (Healthcare Information System), Pharmacy Information System and BPOC (Barcode Point of Care) unit directed by a task management system, according to invention principles.

FIG. 2 shows medication administration related task flow in a system involving HIS (Healthcare Information System) 51, Pharmacy Information System 41 and BPOC (Barcode Point of Care) unit 22 in mobile point of care unit 12 directed by a task management system. Units 51 and 41 are integrated with Bar code Point of Care system (BPOC) 22 resident on a handheld device (such as a PDA), a mobile computer or workstation, or on a computer located in a patient room, for example. Pharmacy Information system 41 enables a user to configure Reminder messages to be associated with a particular drug or drugs by entering information in a repository (database) in system 41 or repository 17 (FIG. 1). A user of BPOC system 22 is also able to determine, based on user role, whether Reminder messages are to be displayed. Specifically, Pharmacy Information system 41 enables a user to configure Reminder messages to be associated with a particular drug or drugs as well as an appropriate timeframe for a reminder message to be generated and provided to a clinician and whether a reminder message is to repeat on a user selectable particular schedule. A Reminder message reminds a clinician to perform a particular post-administration task concerning a particular medication following administration of the particular medication to a patient.

The system prompts a user to enter Reminder messages to be associated with a particular medication via a display image prompt or acquires data automatically associating Reminder messages with corresponding medication from an information source. Reminder messages are automatically displayed to a user of BPOC system 22 in response to a medication order being entered in the pharmacy system, opening a medication profile or selecting a medication for administration, for example, without action being required by a pharmacist or nurse. Reminder messages may be predetermined and either medication specific or not medication specific), such as, "Hold Medication for Systolic Blood Pressure Less Than 100 or Heart Rate Less Than 60", or "Caution, Contact Precautions"/"LATEX Allergy"/"AFB Isolation". Further, Reminder message characteristics may be configured so that a Reminder message needs to be viewed by a BPOC system 22 user (i.e., in a mandatory view) or may be optionally viewed so a Pharmacist or nurse is able to turn a Reminder message on or off. A Reminder message may also be requested by a BPOC user. A BPOC user may also associate a specific medication order and/or patient with, a user entered free text Reminder message or an automatically dynamically generated Reminder message. A Reminder message may be a personal reminder (for a specific user) or a reminder that all BPOC users view concerning a specific medication/patient, for example. A Reminder message may also be requested by a Pharmacist using Pharmacy Information System 41 and may be a predetermined (medication specific) reminder or a user entered free text Reminder message or an automatically dynamically generated Reminder message that a pharmacist wishes to associate with a specific medication order and/or patient. Further, Reminder messages may not be in a drug database and may be assigned by a nurse or pharmacist "On the Fly" (dynamically).

Pharmacy Information system 41 processes an order for a drug with a Reminder message associated with it, to be administered to a particular patient. During an order entry process, a user is able to initiate a query to determine if a Reminder message is associated with a candidate drug for order and to view such a Reminder message. Additionally, if no Reminder message is associated with a drug, a user is able to associate a Reminder message with a drug order "on the fly" (dynamically).

In FIG. 2, an order for a drug is received by Pharmacy Information system 41 from a CPOE (computerized order entry system) in HIS 51. Information indicating an order entered by a pharmacist via Pharmacy Information system 41 is also conveyed to update order entry records in HIS 51. Information indicating orders validated by a pharmacist 41, is communicated to BPOC system 22. Further, an order may be initiated via BPOC system 22 and data indicating such an order is communicated to update order records in Pharmacy Information system 41. In response to a user employing Bar code Point of Care (BPOC) system 22 to open a profile for a patient (or selecting a medication for administration, for example), a visual indicator appears in a display image indicating orders for medication to be administered to a patent which have an associated Reminder message. A user is able to click on a visual indicator associated with a Reminder message to view the Reminder message.

In step 209 (FIG. 2), upon a user administering a drug to a patient in response to a received order for the drug administration and the drug having an associated reminder message, BPOC system 22 automatically, transparently and seamlessly, schedules reminder messages 213, 217 and 223 to be provided to the user at one or more particular times. If a user administers a medication which does not have an associated Reminder message, the user is able to manually associate a Reminder message with a particular medication administration occurrence. Reminder message 213 needs to be viewed by a BPOC system 22 user (i.e., in a mandatory view). Reminder message 217 may be optionally viewed and a Pharmacist or nurse is able to turn Reminder message 217 on or off. Reminder message 223 is entered by a BPOC user as a free text Reminder message. Reminder messages 213, 217 and 223 are provided in step 233 as a personal reminder (for a specific user) or a reminder that all BPOC users view concerning a specific medication/patient. Reminder messages 213, 217 and 223 are presented on a worklist of a user at an appropriate due time.

If user interface 26 (FIG. 1) in step 229 prompts a user to enter a response to a Reminder messages 213, 217 or 223 via a user worklist, a user enters response data in step 231. In step 227, the user addresses and documents the reminder message on their Worklist or selects to postpone the reminder message so they can address and document the reminder message at a later time. Upon entry of response data or if no prompt is provided, medication is administered to a patient (and administration is documented). Data representing the documented medication administration is communicated to HIS 51 from BPOC system 22. Similarly, data representing the Reminder message associated with the documented medication administration is also communicated to HIS 51 and to a user via email, a pager, PDA or notebook from BPOC system 22.

Figure 3:
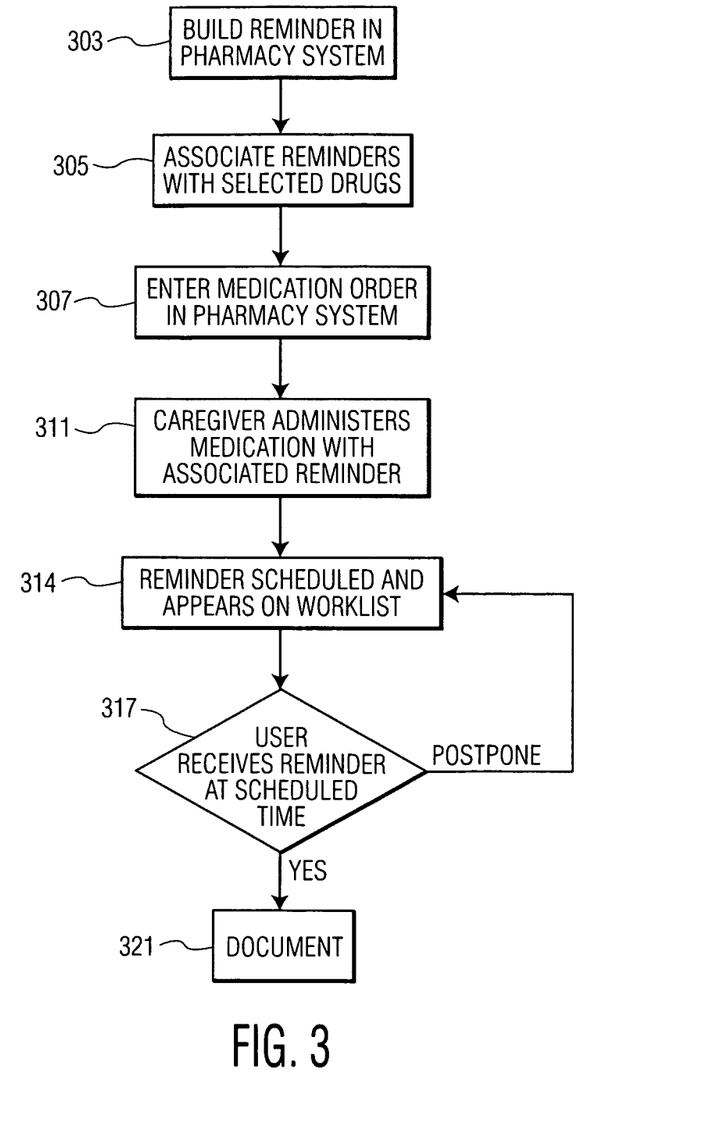
FIG. 3 shows flowchart of reminder message processing directed by a task management system, according to invention principles.

FIG. 3 shows a flowchart of reminder message processing performed by system 10 (FIG. 1) directed by a task management system (workflow processor 34 and Reminder processor 27). In step 303 a user employs Reminder processor 27 and display images provided by user interface 26 to configure Reminder messages and associates the messages in step 305 with medications in a repository used by Pharmacy Information System 41. For example, a user configures Reminder message "Remove Patch for 12 hours—overnight" and associates this message with the medication Nitroglycerin. The user further determines a time duration indicating an action associated with the Reminder message is to be performed 6 hours post medication administration.

In step 307, in response to an order being entered via an order entry system in Pharmacy information system 41 (or via an order entry system in HIS 51) and being received by Pharmacy information system 41 for Nitroglycerin to be administered to a patient, Reminder processor 27 automatically associates the received order with the Reminder message "Remove Patch for 12 hours—overnight". In response to a nurse administering Nitroglycerin to a patient using BPOC system 22 in step 311, workflow processor 34 automatically and transparently in step 314, schedules the Reminder message "Remove Patch for 12 hours—overnight" to be added to a clinician (e.g., a nurse) worklist 6 hours after the administration. In step 317, the Reminder message "Remove Patch for 12 hours—overnight" appears on the clinician's worklist Six hours after administration of the Nitroglycerin. This Reminder message is also displayed on a clinical workstation in HIS 51. The clinician either performs the task indicated in the Reminder message and documents the performance in step 321 or postpones the reminder message which initiates re-scheduling it in step 314 for a later time.

System 10 stores messages in repository 17 or in a drug database in HIS 51 or in Pharmacy information system 41 for use by the reminder notification process of FIG. 3. The Reminder messages may relate to specific tasks or follow up actions that are required for a particular medication. A Reminder message may comprise, for example, "Warfarin—Check INR/Call Physician for Daily Order" set to be triggered at a specific time of day in response to an order message being entered under the warfarin entry in a drug database. A further Reminder message may comprise, for example, "Nitroglycerin Patch—Remove for 12-Hours Overnight" set to be triggered in the evening when nitroglycerin patches are frequently removed in response to an order message being entered under the nitroglycerin entry in the drug database. Another Reminder message may comprise, for example, "Vancomycin Trough—Draw trough level prior to administering next dose" set to be triggered just prior to administering the next dose of vancomycin, when it is clinically correct to draw a trough level in response to an order message being entered under the Vancomycin entry in the drug database. It is not possible to correctly adjust the dose of medication (if necessary) based upon a trough level that was measured at an incorrect time.

Reminder messages may be set, using Reminder processor 27, to alert a clinician using BPOC system 22 via a "Pop-up" display image window. The Reminder messages may be communicated or displayed to a clinician at specific times, and may recur (e.g., Daily, weekly, monthly, etc.), for a specific number of occurrences, or for a specific period of time. For example, the Reminder message "Patient is NPO X 24 Hours/Call Physician to Update Status" is set to recur on a daily basis or it may be set to display one time only. Further, the Reminder messages may be communicated or displayed to a clinician during specific tasks such as administration tasks, in response to a medication profile being opened. A Reminder message may also be provided to a clinician in response to completion of administration of an IV solution. For example, a Reminder message may be displayed to a user after an estimated time of completion of administration of an IV infusion based upon infusion start time and infusion flow rate. Alternatively, a message may also be triggered in response to BPOC system 22 receiving information from a "smart" infusion device or in response to certain events such as patient admission or transfer or when specific sets of treatments are ordered, for example.

BPOC system 22 enables a user to select to view Reminder messages for patients they are responsible for or to select a subset of particular patients and to optionally add additional patient Reminder messages to view. Reminder processor 27 may require a user of BPOC system 22 to enter data in response to a particular Reminder message in response to configuration data associating particular Reminder messages with particular requirements. Reminder processor 27 may also forward particular Reminder messages to HIS 51, a clinician pager or to a clinician via email, for example, to notify workers of a required action. In operation, if Reminder message "Warfarin—Check INR/Call Physician for Daily Order" is presented in a BPOC system 22 display, for example, reminder processor 27 forwards corresponding message "Daily Order for Warfarin is Needed" to a prescribing clinician in HIS 51. Further, a clinician may respond to a Reminder message by indicating a preference to be reminded again with the same message in a specified period of time or to forward the Reminder message to another user who is now caring for the patient. Reminder messages may be viewed by a user from a central monitoring workstation in BPOC system 22 and a clinician may set the monitoring workstation to present messages during specific times of the day. The monitoring workstation also allows Reminder messages to be viewed outside of a patient specific profile in a display image including a user selectable link to the patient profile that may be accessed from the monitoring workstation.

In response to opening a patient profile using a workstation in BPOC system 22, icons representing Reminder messages that are assigned to the patient are displayed as "sticky-notes". A clinician may click on these icons to display the Reminder messages that may be presented for access by authorized users occupying specific roles or specific users of BPOC system 22. A respiratory therapist Reminder message is only accessible by a user occupying a respiratory therapist role, for example. Further, a specific indicator is used by Pharmacy Information System 41 and by BPOC system 22, is set when a medication is stocked in an automated dispensing cabinet, supplied by a pharmacy or provided to a dispensing cart, for example. A Reminder message is generated by reminder processor 27 in response to the indicator being set, that displays to a user of BPOC system 22 the location of the newly stocked medication. The location of medications may change based upon patient location and in response, reminder processor 27 automatically updates data indicating current location of medications. Reminder processor 27 is configured to generate Reminder messages to prompt worker actions at specific times such as in response to a user opening a particular patient profile, a time of medication administration or user opening of a Reminder message window. A user of BPOC system 22 workstation may enter a Reminder message that is stored for later re-call at a specific time such as at the time of a worker shift change and may enter notes configured to be displayed on demand. Image displays are also stored and incorporated in to notepad entries or specific data within a BPOC system 22 application and may be forwarded to the notepad with time, date and user information.

Figure 4:
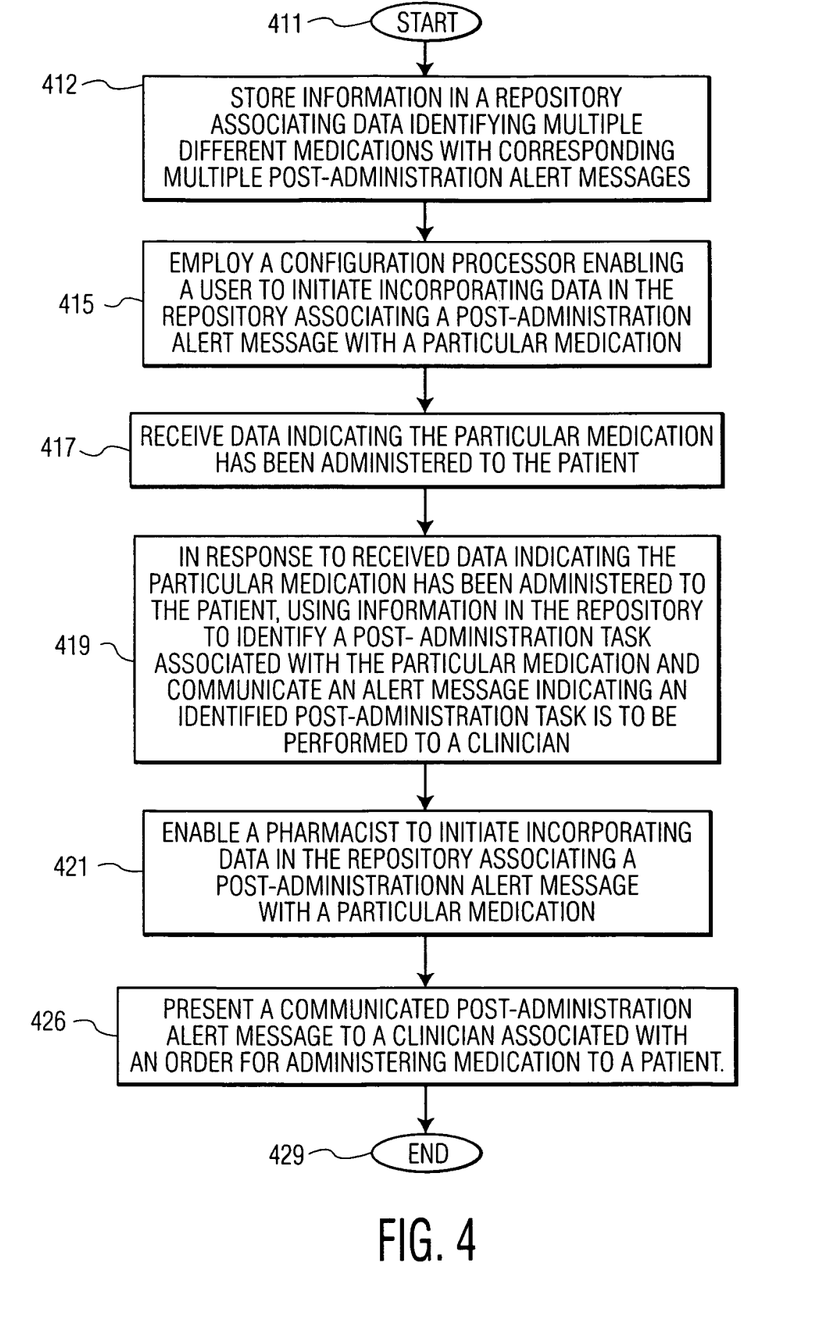
FIG. 4 shows a flowchart of a process performed by a task management system for informing a clinician of medication administration related tasks to be performed, according to invention principles.

FIG. 4 shows a flowchart of a process performed by task management system 10 for informing a clinician of medication administration related tasks to be performed. In step 412 following the start at step 411, system 10 stores information in repository 17 that associates data identifying multiple different medications with corresponding multiple post-administration alert messages. An individual alert message notifies one or more clinicians of a particular post-administration task to be performed concerning a particular medication following administration of the particular medication to a patient. In step 415, a configuration processor within Pharmacy Information System 41 enables a user to store data in repository 17 associating a post-administration alert message with a particular medication.

In step 417, Pharmacy interface 29 receives order data associating the particular medication with the patient from pharmacy information system 41. Further, input processor 15 receives data indicating the particular medication has been administered to the patient. Workflow processor 34, in step 419 in response to received data indicating the particular medication has been administered to the patient, uses information in repository 17 to identify a post-administration task associated with the particular medication and communicates an alert message, via interface 19 to a clinician, indicating an identified post-administration task is to be performed. Workflow processor 34 automatically adds data indicating the identified post-administration task is to be performed for the patient to a task list of the clinician together with a scheduled time for performance of the identified post-administration task in response to received order data. Workflow processor 34 also automatically compiles a task list including pre-administration and post-administration tasks associated with the particular medication in response to received data indicating scheduled medication administration for the patient. Workflow processor 34 determines a clinician role in response to predetermined information and the entered login information and automatically compiles the task list in response to a determined role.

In step 421, the configuration processor enables a pharmacist to initiate incorporating data in repository 17 associating a post-administration alert message with a particular medication. In step 426, the task management system is accessed via a mobile point of care unit workstation. A user interface 26 (or other reproduction device) in mobile point of care system 12 including bar code point of care system 22 presents the communicated post-administration alert message to a clinician associated with an order for administering medication to a patient and indicating the identified post-administration task to be performed for a patient for viewing by the clinician. User interface 26, located on a workstation in mobile point of care unit 12 at a point of care, initiates generation of data representing at least one display image enabling a clinician to access a task list in response to entered login information. The at least one display image also enables a clinician to postpone the addition of data indicating the identified post-administration task to the task list of the clinician. Authorization processor 39 enables access by a clinician to the task list in response to entered login information. The process of FIG. 4 terminates at step 429.

The systems and processes of FIGS. 1-4 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system is used by nurses and other clinicians responsible for medication administration who utilize a BPOC system and enables clinicians to schedule dynamic generation of reminder messages whenever they are required that alert a user of important follow-up tasks to be performed for a patient. The processes and applications may, in alternative embodiments, be located on one or more (e.g., distributed) processing devices accessing a network linking the elements of FIG. 1. Further, any of the functions and steps provided in FIGS. 1-4 may be implemented in hardware, software or a combination of both and may reside on one or more processing devices located at any location of a network linking the elements of FIG. 1 or another linked network, including the Internet.

What is claimed is:

1. A task management system for informing a clinician of medication administration related tasks to be performed, comprising:
   a repository of information associating data identifying a plurality of different medications with a corresponding plurality of post-administration alert messages, an individual alert message being for notifying a clinician of a particular post-administration task to be performed concerning a particular medication following administration of said particular medication to a patient;
   a pharmacy information system including a configuration processor device enabling a pharmacist to initiate incorporating data in said repository associating a post-administration alert message with a particular medication as well as with times for a post-administration alert message to be generated and provided to a clinician and enabling a pharmacist to dynamically associate a post-administration alert message that is not in a medication database with a particular medication and configured to automatically generate the post-administration alert message for an order for the particular medication for presentation on a mobile point-of-care medication administration system;
   a communication interface presenting the post-administration alert message as a pop-up display window on a graphic user interface of a mobile point-of-care medication device, the post-administration alert message being automatically presented on the graphic user interface upon one of the following: an order for the particular administration is entered for the patient, the particular medication is selected for administration for the patient, or a medication profile for the particular medication is opened;
   an input processor device receiving data indicating said particular medication has been administered to said patient;
   a workflow processor device processing data to determine tasks to add to or remove from a task list or to modify tasks incorporated on, or for incorporation on, a task list and for, in response to received data indicating said particular medication has been administered to said patient, using information in said repository to identify a post-administration task associated with said particular medication and automatically adding data indicating an identified post-administration task to be performed to a task list of a clinician; and the mobile point-of-care medication device presenting said identified post-administration task and task list of said clinician and a post-administration alert message to said clinician for viewing by a user.

2. A system according to claim 1, wherein
said configuration processor device enables the pharmacist to configure whether the post-administration alert message is to repeat on a user selectable particular schedule.

3. A system according to claim 1, including
a pharmacy interface receiving order data concerning said patient from a pharmacy information system, said order data associating said particular medication with said patient and
said workflow processor device automatically adds data indicating said identified post-administration task is to be performed for said patient to said task list in response to received order data.

4. A system according to claim 1, including
a mobile point of care unit enabling a user to dynamically associate a post-administration alert message with administration of a particular medication to a particular patient wherein said task management system is accessible via a workstation on said mobile point of care unit.

5. A system according to claim 1, including
a user interface located on a workstation at a point of care for initiating generation of data representing at least one display image enabling a clinician to access said task list in response to entered login information.

6. A system according to claim 5, including
an authorization processor enabling access by the clinician to said task list in response to entered login information.

7. A system according to claim 6, wherein
said workflow processor device determines a clinician role in response to predetermined information and said entered login information and automatically compiles said task list in response to a determined role.

8. A system according to claim 1, wherein
said workflow processor device automatically adds said data indicating said identified post-administration task to be performed to said task list together with a scheduled time for performance of said identified post-administration task.

9. A system according to claim 1, wherein
said workflow processor device automatically compiles the task list to include pre-administration and post-administration tasks associated with said particular medication in response to received data indicating scheduled medication administration for said patient.

10. A system according to claim 1, including
a user interface located on a workstation at a point of care initiating generation of data representing at least one display image enabling a clinician to postpone the addition of data indicating said identified post-administration task to said task list of said clinician.

11. A task management system for informing a clinician of medication administration related tasks to be performed, comprising:
a repository of information associating data identifying a plurality of different medications with a corresponding plurality of post-administration alert messages, an individual alert message notifying a clinician of a particular post-administration task to be performed concerning a particular medication following administration of said particular medication to a patient;
a pharmacy information system including a configuration processor device enabling a user to initiate incorporating data in said repository associating a post-administration alert message with a particular medication as well as with times for a post-administration alert message to be generated and provided to a clinician and enabling a pharmacist to dynamically on-the-fly, associate a post-administration alert message that is not in a medication database with a particular medication and configured to automatically generate the post-administration alert message for an order for the particular medication for presentation on a mobile point-of-care medication administration system;
a communication interface presenting the post-administration alert message as a pop-up display window on a graphic user interface of a mobile point-of-care medication device, the post-administration alert message being automatically presented on the graphic user interface upon one of the following: an order for the particular administration is entered for the patient, the particular medication is selected for administration for the patient, or a medication profile for the particular medication is opened;
an input processor device receiving data indicating said particular medication has been administered to said patient;
a workflow processor device, in response to received data indicating said particular medication has been administered to said patient, using information in said repository to identify a post-administration task associated with said particular medication and communicating an alert message indicating an identified post-administration task is to be performed to a clinician; and
the mobile point-of-care medication device presenting the communicated post-administration alert message to the clinician indicating said identified post-administration task to be performed for a patient for viewing by the clinician.

12. A system according to claim 11, wherein
said configuration processor device enables the pharmacist to configure whether a post-administration alert message is to repeat on a user selectable particular schedule.

13. A task management system for informing a clinician of medication administration related tasks to be performed, comprising:
a repository of information associating data identifying a plurality of different medications with a corresponding plurality of post-administration alert messages, an individual alert message being for notifying a clinician of a particular post-administration task to be performed concerning a particular medication following administration of said particular medication to a patient;
a pharmacy information system including a configuration processor device enabling a user to initiate incorporating data in said repository associating a post-administration alert message with a particular medication as well as with times for a post-administration alert message to be generated and provided to a clinician and enabling a pharmacist to dynamically associate a post-administration alert message that is not in a medication database with a particular medication and configured to automatically generate the post-administration alert message for an order for the particular medication for presentation on a mobile bar code point-of-care system;

a communication interface presenting the post-administration alert message as a pop-up display window on a graphic user interface of a mobile bar code point-of-care device, the post-administration alert message being automatically presented on the graphic user interface upon one of the following: an order for the particular administration is entered for the patient, the particular medication is selected for administration for the patient, or a medication profile for the particular medication is opened;

an input processor device receiving data indicating said particular medication has been administered to said patient;

a workflow processor device, in response to received data indicating said particular medication has been administered to said patient, using information in said repository to identify a post-administration task associated with said particular medication and communicating an alert message indicating an identified post-administration task is to be performed to a clinician; and the mobile bar code point-of-care device presenting an identified post-administration alert message to a clinician associated with an order for administering medication to a patient.

14. A computerized task management method for informing a clinician of medication administration related tasks to be performed, comprising:

associating data for a particular medication with one or more post-administration alert messages, each post-administration alert message notifying a clinician of a particular post-administration task to be performed concerning the particular medication following administration of said particular medication to a patient;

receiving data indicating the particular medication has been administered to said patient;

in response to received data indicating said particular medication has been administered to said patient, determining one or more tasks to add to a task list for the clinician using information in said repository to identify a post-administration task associated with said particular medication and automatically adding data indicating an identified post-administration task to be performed to a task list of the clinician; and upon receiving data including the particular medication has been administrated, automatically generating the post-administration alert message for an order for the particular medication, the post-administration alert message being generated for presentation on a mobile point-of-care medication administration system; and presenting the post-administration alert message as a pop-up display window on a graphic user interface of a mobile point-of-care medication device, the post-administration alert message being automatically presented on the graphic user interface upon one of the following: the order for the particular administration is entered for the patient, the particular medication is selected for administration for the patient, or a medication profile for the particular medication is opened.

* * * * *